(12) United States Patent
Ishihara (10) Patent No.: US 8,343,037 B2
(45) Date of Patent: Jan. 1, 2013

(54) ENDOSCOPE APPARATUS AND ENDOSCOPE-IMAGE RECORDING METHOD

(75) Inventor: Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 770 days.

(21) Appl. No.: 12/530,904

(22) PCT Filed: Mar. 13, 2008

(86) PCT No.: PCT/JP2008/054630
§ 371 (c)(1),
(2), (4) Date: Sep. 11, 2009

(87) PCT Pub. No.: WO2008/111646
PCT Pub. Date: Sep. 18, 2008

(65) Prior Publication Data
US 2010/0113876 A1 May 6, 2010

(30) Foreign Application Priority Data
Mar. 13, 2007 (JP) ................................. 2007-063823

(51) Int. Cl.
*A61B 1/04* (2006.01)
(52) U.S. Cl. .............................. 600/117; 396/17; 348/65
(58) Field of Classification Search ................. 600/117; 396/17; 348/65
See application file for complete search history.

(56) References Cited

U.S. PATENT DOCUMENTS

| 2006/0009679 A1* | 1/2006 | Ito et al. ......................... 600/117 |
| 2007/0249901 A1* | 10/2007 | Ohline et al. .................. 600/117 |
| 2008/0058594 A1* | 3/2008 | Xie et al. ....................... 600/109 |

FOREIGN PATENT DOCUMENTS

| JP | SHO-55-116330 | 9/1980 |
| JP | HEI-6-90899 | 4/1994 |
| JP | 7-171088 | 7/1995 |
| JP | 8-280604 | 10/1996 |
| JP | 2004-105725 | 4/2004 |

* cited by examiner

Primary Examiner — Clayton E Laballe
Assistant Examiner — Fang-Chi Chang
(74) Attorney, Agent, or Firm — Scully Scott Murphy & Presser, PC (57) ABSTRACT

An endoscope apparatus including an insertion portion for insertion into a body cavity; an image-acquisition unit disposed at a tip thereof that acquires an image of the inside of the body cavity; an insertion-length measuring unit disposed at a base end of the insertion portion that measures an insertion length of the insertion portion inside the body cavity; a storage unit that stores the image acquired by the image-acquisition unit in association with the insertion length measured by the insertion-length measuring unit; a following decision unit that determines whether insertion movement at the tip follows insertion movement at the base end; and a correcting unit that corrects the insertion length of the insertion portion associated with the acquired image to cancel a change in the insertion length measured in a non-following period on the basis of the result of that determination.

9 Claims, 9 Drawing Sheets

ENDOSCOPE APPARATUS AND ENDOSCOPE-IMAGE RECORDING METHOD

TECHNICAL FIELD

The present invention relates to an endoscope apparatus and an endoscope-image recording method.

BACKGROUND ART

There is a known endoscope in the related art in which marks indicating the distance from the tip of an insertion portion are provided on the outer surface of the insertion portion for ascertaining the insertion depth of the insertion portion of the endoscope, and which is equipped with a reading device for reading these marks (for example, refer to Patent Documents 1 to 3).

Patent Document 1: Japanese Unexamined Patent Application, Publication No. SHO-55-116330
Patent Document 2: Japanese Unexamined Patent Application, Publication No. HEI-6-90899
Patent Document 3: Japanese Unexamined Patent Application, Publication No. 2004-105725

DISCLOSURE OF INVENTION

According to these Patent Documents 1 to 3, the insertion length of the insertion portion of the endoscope inside the body cavity is detected by a camera, or from the amount of rotation of a motor etc., at the base end of the insertion portion. In this case, the base end of the insertion portion is disposed outside a body cavity.

The present invention is to provide an endoscope apparatus and an endoscope-image recording method in which it is possible to store each position on the inner wall of the body cavity in accurate association with the insertion length, even in cases where the insertion length detected outside the body cavity does not correspond to the amount of movement of the tip of the insertion portion relative to the inner wall of the body cavity, due to factors such as changes in the frictional force between the insertion portion and the inner wall of the body cavity, elasticity of the inner wall of the body cavity, and so forth.

A first aspect of the present invention is an endoscope apparatus including an insertion portion for insertion into a body cavity; an image-acquisition unit that acquires an image of the inside of the body cavity at a tip of the insertion portion; an insertion-length measuring unit that is disposed at a base end of the insertion portion and that measures an insertion length of the insertion portion inside the body cavity; a storage unit that stores the image acquired by the image-acquisition unit in association with the insertion length measured by the insertion-length measuring unit; a following decision unit that determines whether insertion movement at the tip of the insertion portion follows insertion movement at the base end of the insertion portion; and a correcting unit that corrects the insertion length of the insertion portion associated with the image acquired by the image-acquisition unit so as to cancel a change in the insertion length measured by the insertion-length measuring unit in a period where the insertion movement at the tip does not follow the insertion movement at the base end, on the basis of a determination result from the following decision unit.

According to the first aspect of the present invention, by inserting the insertion portion inside the body cavity and operating the image-acquisition unit, an image of the interior of the body cavity located in the vicinity of the tip of the insertion portion is acquired. On the other hand, the insertion length of the insertion portion is measured by operating the insertion-length measuring unit disposed at the base end of the insertion portion. Then, the acquired image is stored in the storage unit in association with the measured insertion length.

In this case, according to the first aspect of the present invention, by operating the following decision unit, it is determined whether or not the insertion movement at the base end of the insertion portion and the insertion movement at the tip of the insertion portion follow each other. By operating the correcting unit in a period where it is determined that the insertion movement at the base end of the insertion portion and the insertion movement at the tip of the insertion portion do not follow each other, the insertion length is corrected so that the change in the insertion length measured by the insertion-length measuring unit is cancelled.

One example of a situation where the insertion movement at the base end of the insertion portion and the insertion movement at the tip of the insertion portion do not follow each other is when the tip of the insertion portion becomes attached to the inner wall of the body cavity surrounding the tip of the insertion portion, and the insertion portion and the inner wall of the body cavity move together, which as a result, means that no relative movement occurs between the two. In this case, even though the insertion length of the base end, measured by the insertion-length measuring unit, changes, the tip of the insertion portion and the inner wall of the body cavity do not more relative to each other, and therefore, there is no change in the images acquired by the image-acquisition unit.

Thus, by operating the correcting unit in a period where the insertion movement at the tip of the insertion portion does not follow the insertion movement at the base end in this way, even if the insertion length at the base end changes, the change is cancelled, thus being treated as if there is no change. Accordingly, it is possible to prevent the problem of associating a plurality of insertion lengths with the same image obtained by performing image acquisition at the same position.

Therefore, because the acquired image is precisely associated with the insertion length of the insertion portion, by checking the stored information afterwards, it is possible to accurately identify the position of an affected area contained in the image, such as inflammation or a tumor.

In the first aspect described above, the following decision unit may include a load detecting unit that detects a load exerted in the longitudinal direction of the insertion portion, and after movement of the insertion portion in the longitudinal direction stops, when movement resumes in the same direction as the movement, or in the reverse direction thereto, and the load detected by the load detecting unit becomes a peak value, a period from resumption of movement of the insertion portion until the load exceeds the peak value may be determined to be a period where the insertion movement at the tip does not follow the insertion movement at the base end.

When the insertion portion is stopped after moving in the longitudinal direction in the body cavity, the frictional force between the outer surface of the insertion portion and the inner wall of the body cavity momentarily changes from the kinetic frictional force to zero. Then, when the insertion portion resumes motion and the load detected by the load detecting unit exceeds the peak value, the frictional force between the outer surface of the insertion portion and the inner wall of the body cavity changes from the static frictional force to the kinetic frictional force. Because the maximum static frictional force is larger than the kinetic frictional force, the load exerted in the longitudinal direction of the insertion portion also changes in accordance therewith.

Therefore, the load exerted in the longitudinal direction of the insertion portion is detected by operating the load detecting unit. Then, if the load detected after resuming motion is the peak value, at the instant the load exceeds the peak value and falls, it can be detected that the friction between the insertion portion and the inner surface of the body cavity has changed from static friction to kinetic friction. As a result, the period until the load exceeds the peak value after motion is resumed is determined as being the period where the insertion movement at the tip does not follow, thereby making it possible to prevent the problem of multiple insertion lengths being associated with the same image obtained by performing image acquisition at the same position.

Accordingly, because the acquired image is precisely associated with the insertion length of the insertion portion, by checking the stored information afterwards, it is possible to accurately identify the position of an affected area contained in the image, such as inflammation or a tumor.

In the above-described configuration, the following decision unit may detect resumption of movement of the insertion portion when the sign of the load detected by the load detecting unit changes.

In cases such as the insertion portion becoming loosened from the inner wall of the body cavity from the base end to the tip of the insertion portion, in some cases, movement of the tip of the insertion portion may not be resumed even though the insertion length measured by the insertion-length measuring unit changes in the decreasing direction. Therefore, by detecting that motion of the insertion portion has resumed, that is to say, reversed, when the sign of the load detected by the load detecting unit has changed, it is possible to detect resumption of motion of the insertion portion more accurately.

In the first aspect described above, the following decision unit may compare images consecutively acquired by the image-acquisition unit, and if, as a result of the comparison, the images do not change, when the insertion length measured by the insertion-length measuring unit changes, may determine that the insertion movement at the tip of the insertion portion does not follow the insertion movement at the base end of the insertion portion.

In the period when the insertion movement at the tip of the insertion portion does not follow the insertion movement at the base end of the insertion portion, the tip of the insertion portion becomes attached to the inner wall of the body cavity and moves together therewith. Therefore, there is no change in the images sequentially acquired by the image-acquisition unit. With this configuration, it is possible to more accurately cancel the change in insertion length during the period when the tip of the insertion portion does not move relative to the inner wall of the body cavity because the insertion movements do not follow each other.

In the first aspect described above, the image-acquisition unit may be provided with a side-view optical system that collects light from radially outward of the insertion portion.

By acquiring the light collected via the side-view optical system, it is possible to obtain an image directly facing the inner wall of the body cavity. By storing the image obtained in this way in association with the insertion length, it is possible to more accurately identify the position of an affected area.

A second aspect of the present invention is an endoscope-image recording method for storing an image of the inside of a body cavity, which is acquired by an image-acquisition unit at the tip of an insertion portion that is inserted inside the body cavity, in association with an insertion length of the insertion portion inside the body cavity, which is measured at the base end of the insertion portion, including determining whether insertion movement at the tip of the insertion portion follows insertion movement at the base end of the insertion portion; and correcting the insertion length associated with the acquired image so as to cancel a change in the insertion length measured in a period where the insertion movement at the tip does not follow the insertion movement at the base end, on the basis of the determination result.

The second aspect described above may further include detecting a load exerted in the longitudinal direction of the insertion portion; and after movement of the insertion portion in the longitudinal direction has stopped, when movement resumes in the same direction as the movement, or in the reverse direction thereto, and the detected load becomes a peak value, determining that a period from resumption of movement of the insertion portion until the load exceeds the peak value is a period in which the insertion movement at the tip does not follow the insertion movement at the base end.

In the configuration described above, resumption of movement of the insertion portion may be detected when the sign of the detected load changes.

In the configuration described above, consecutively acquired images may be compared, and if, as a result of the comparison, the images do not change, when the measured insertion length changes, it may be determined that the insertion movement at the tip of the insertion portion does not follow the insertion movement at the base end of the insertion portion.

The present invention affords an advantage in that, even in cases where the insertion length detected outside the body cavity does not correspond to the amount of movement of the tip of the insertion portion relative to the inner wall of the body cavity, it is still possible to accurately associate each position on the inner surface of the body cavity with the insertion length.

EXPLANATION OF REFERENCE SIGNS

X: body cavity
1: endoscope apparatus

2: insertion portion
3: image-acquisition unit
4: insertion-length measuring unit
5: storage unit
8: following decision unit
9: correcting unit
12: conical mirror (side-view optical system)
18: load sensor (load detecting unit)

BEST MODE FOR CARRYING OUT THE INVENTION

An endoscope apparatus 1 according to a first embodiment of the present invention will be described below with reference to FIGS. 1 to 4.

Figure 1:
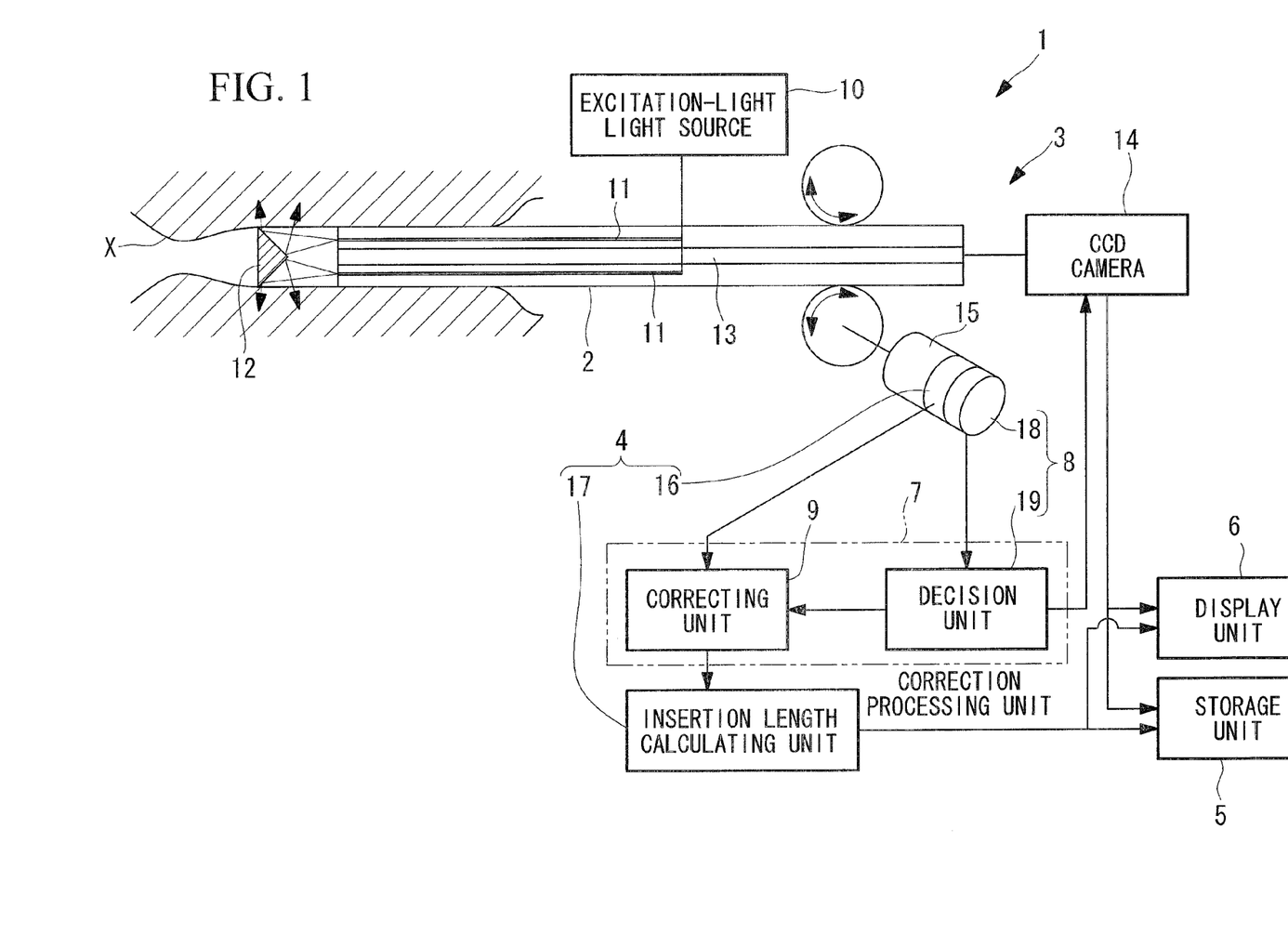
FIG. 1 is an overall configurational diagram showing an endoscope apparatus according to an embodiment of the present invention.

As shown in FIG. 1, the endoscope apparatus 1 according to this embodiment includes an insertion portion 2, an image-acquisition unit 3, an insertion-length measuring unit 4, a storage unit 5, and a display unit 6. The insertion portion 2 is inserted inside a body cavity X. The image-acquisition unit 3 acquires an image of the interior of the body cavity X at the tip of the insertion portion 2. The insertion-length measuring unit 4 measures the insertion length inside the body cavity X at the base end of the insertion portion 2. The storage unit 5 stores an image acquired by the image-acquisition unit 3 in association with the insertion length measured by the insertion-length measuring unit 4. The display unit 6 displays the image acquired by the image-acquisition unit 3 in association with the insertion length measured by the insertion-length measuring unit 4.

The endoscope apparatus 1 according to this embodiment is provided with a correction processing unit 7 that adjusts the association between the image stored in the storage unit 5 and the insertion length. The correction processing unit 7 includes a following decision unit 8 and a correcting unit 9. The following decision unit 8 determines whether or not the insertion movement at the tip follows the insertion movement at the base end of the insertion portion 2. On the basis of the determination result, the correcting unit 9 cancels out a change in the insertion length in a period where the insertion movement is not following at the tip side (hereinafter referred to as non-following period). In other words, it performs correction so that the insertion length of the insertion portion 2 does not change.

The insertion portion 2 has an excitation-light light source 10 connected thereto and is provided with a light guide 11 that conveys excitation light from the excitation-light light source 10 to the tip along the longitudinal direction of the insertion portion 2. A cone-shaped conical mirror (side-view optical system) 12 is also provided at the tip of the insertion portion 2. The conical mirror 12 reflects the excitation light conveyed via the light guide 11 and radiates it outward in the radial direction, and also reflects fluorescence emitted from the inner wall of the body cavity X, introducing the fluorescence into an image guide 13, to be described later. The conical mirror 12 radiates the excitation light conveyed via the light guide 11 around the entire periphery in the circumferential direction. Thus, the conical mirror 12 can take into the image guide 13 a fluorescence image covering the entire circumference of the inner wall of the body cavity X.

The image-acquisition unit 3 includes the image guide 13, which is disposed along the longitudinal direction of the insertion portion 2, and a CCD camera 14 that is connected to the base end of the image guide 13. The fluorescence conveyed via the image guide 13 is acquired by the CCD camera 14. Accordingly, it is possible to obtain a fluorescence image around the entire circumference of the inner wall of the body cavity X.

The insertion-length measuring unit 4 includes an encoder 16 and an insertion-length calculating unit 17. The encoder 16 is provided with a motor 15 that drives the insertion portion 2. The insertion-length calculating unit 17 calculates the insertion length of the insertion portion 2 on the basis of the rotation angle of the motor 15, which is detected by the encoder 16. In other words, the insertion-length calculating unit 17 calculates the insertion length by working out insertion-length increments corresponding to the rotation angle increments of the motor 15 output from the encoder 16 and sequentially sums the insertion-length increments. When the insertion portion 2 is withdrawn from the body cavity X, the rotation angle increment and the insertion-length increment take negative values.

The following decision unit 8 includes a load sensor (load detecting unit) 18 and a decision unit 19. The load sensor 18 is built into the motor 15. The decision unit 19 determines whether or not the insertion movement at the tip follows the insertion movement at the base end of the insertion portion 2 on the basis of changes in the load along the longitudinal direction of the insertion portion 2, detected by the load sensor 18.

Specifically, non-following of the insertion movement at the tip relative to the insertion movement at the base conspicuously occurs when the insertion movement of the insertion portion 2 is reversed.

Figure 2A:
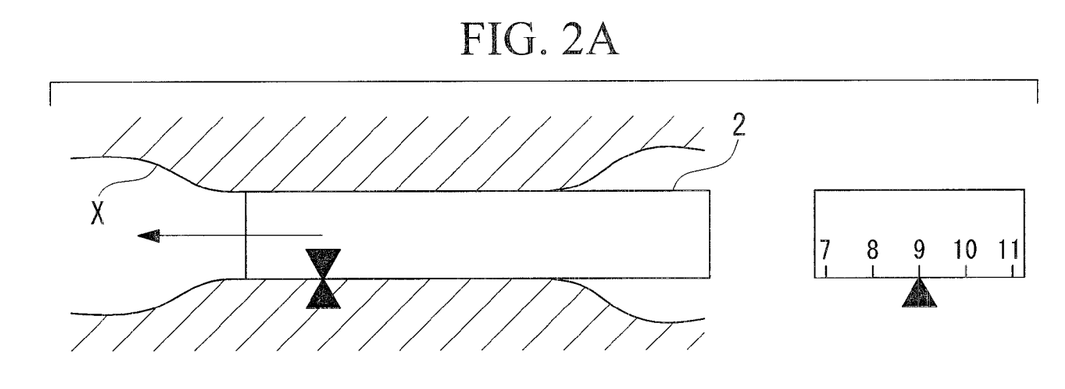
FIG. 2A is a diagram for explaining a reversing movement of the tip of an insertion portion of the endoscope apparatus in FIG. 1.

In other words, as shown in FIG. 2A, during the insertion movement of the insertion portion 2, the outer surface of the insertion portion 2 and the inner surface of the body cavity X move relative to each other while generating kinetic friction. At this time, the load detected by the load sensor 18 is substantially constant, as shown by sign A in FIG. 3. The actual insertion length at the base end of the insertion portion 2 is what is shown at the right in FIGS. 2A, 2B, and 2C.

Figure 2B:
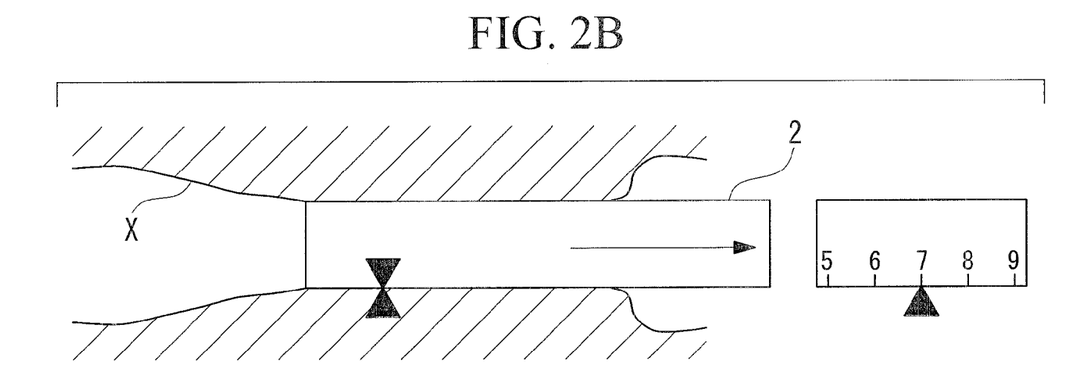
FIG. 2B is a diagram for explaining the reversing movement of the tip of the insertion portion of the endoscope apparatus in FIG. 1.

However, after the insertion movement of the insertion portion 2 is temporarily stopped, even if the insertion movement of the insertion portion 2 is subsequently resumed, in some cases, relative movement of the tip of the insertion portion 2 with respect to the inner surface of the body cavity X does not resume. Therefore, the surgeon must exert a force exceeding the maximum static frictional force generated between the outer surface of the insertion portion 2 and the inner surface of the body cavity X. For example, when the insertion movement of the insertion portion 2 is reversed, the outer surface of the insertion portion 2 and the inner surface of the body cavity X temporarily stop relative to each other, and become joined due to static friction. If the reversing movement is performed thereafter, as shown in FIG. 2B, with the outer surface of the insertion portion 2 and the inner surface of the body cavity X remaining joined, the insertion portion 2 moves, deforming the body cavity X, rather than producing relative movement between the insertion portion 2 and the inner surface of the body cavity X. The insertion length measured by the insertion-length measuring unit 4 shifts backwards by two graduations from the state in FIG. 2A.

Figure 3:
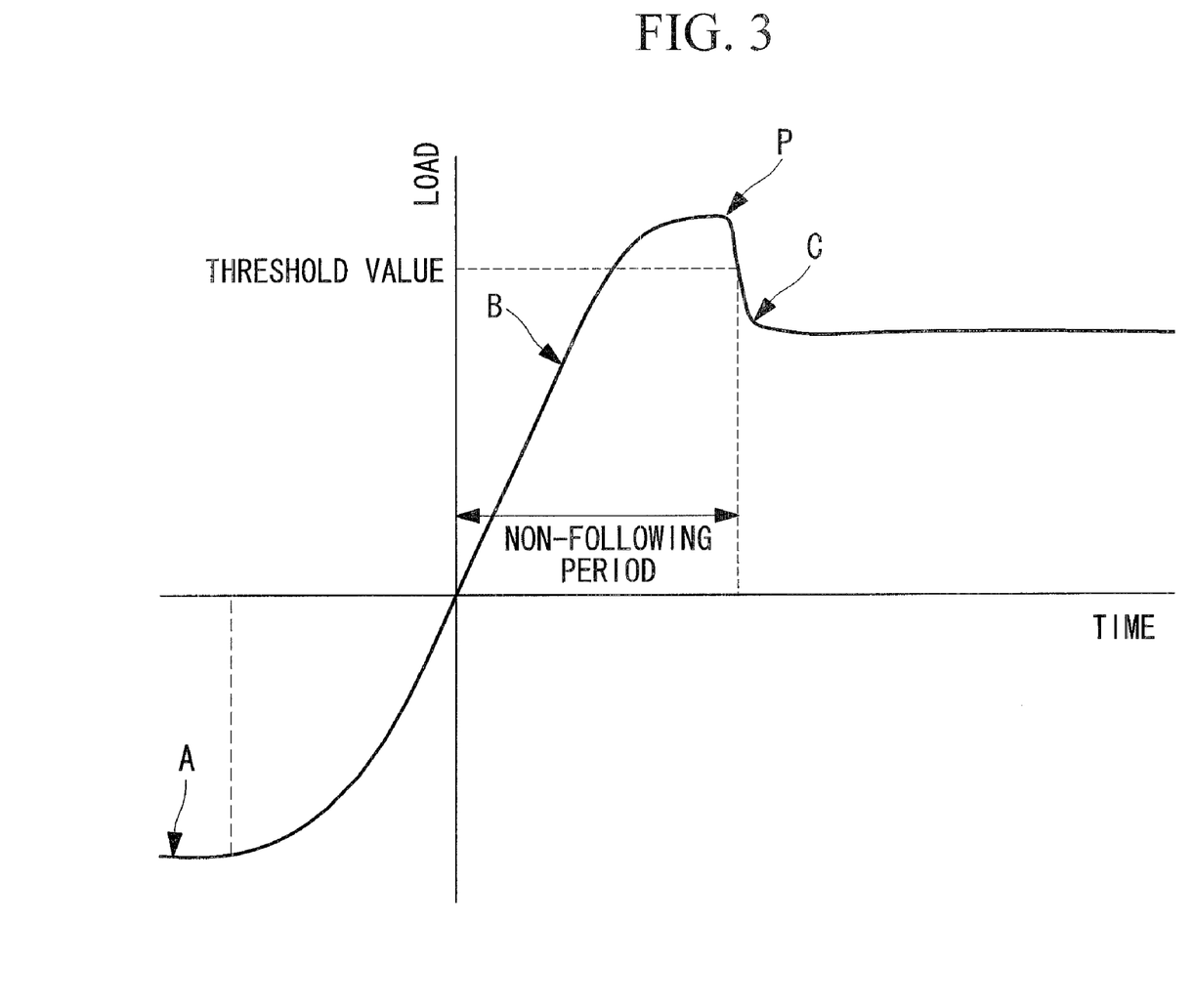
FIG. 3 is a graph showing an example of the load exerted in the longitudinal direction of the insertion portion during the reversing movement in FIGS. 2A, 2B, and 2C.

At this time, the sign of the load detected by the load sensor 18 changes from sign A to sign B, as shown in FIG. 3. Thus, the sign of the load detected by the load sensor 18 reverses, and the absolute value thereof exceeds the absolute value of the load during the insertion movement in the region of sign A and has a peak P.

Figure 2C:
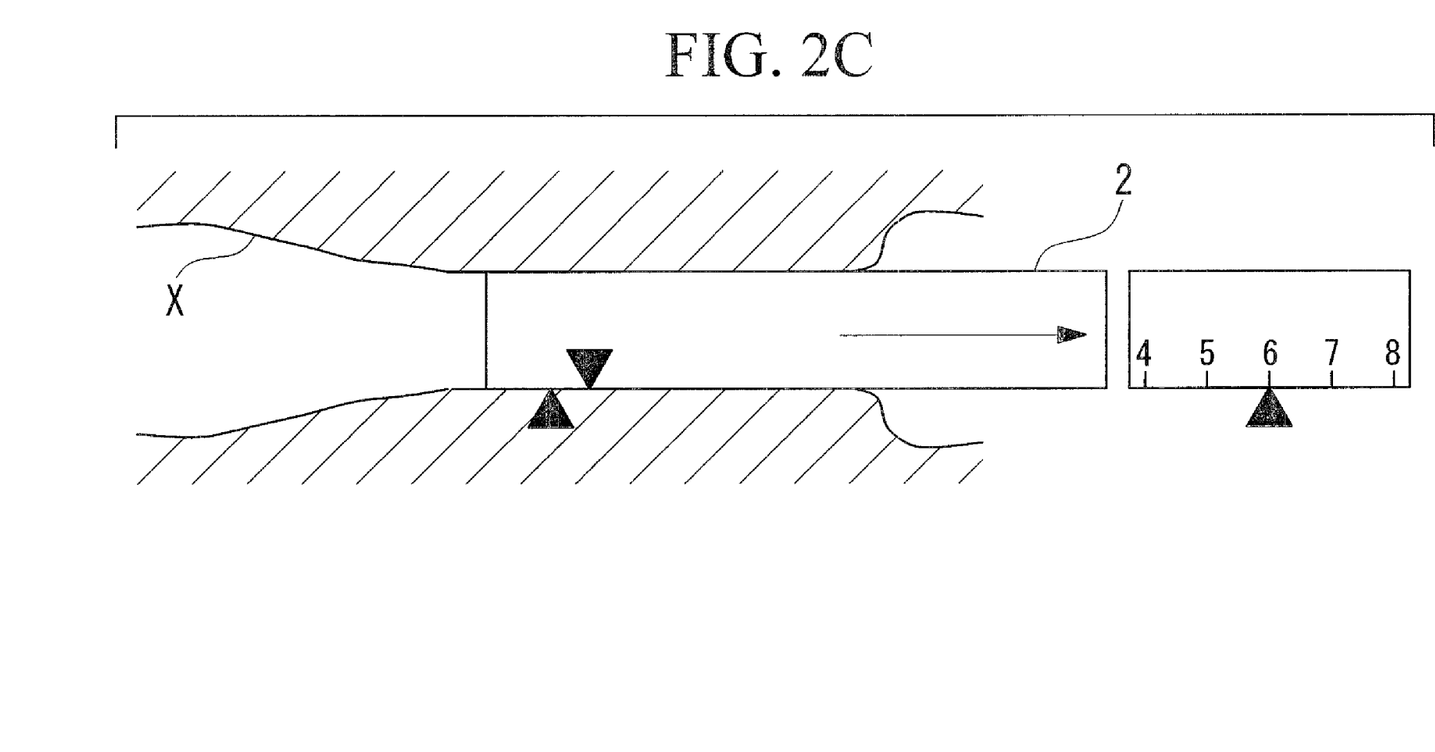
FIG. 2C is a diagram for explaining the reversing movement of the tip of the insertion portion of the endoscope apparatus in FIG. 1.

When the insertion portion 2 is moved further, as shown in FIG. 2C, the joined state of the insertion portion 2 and the inner surface of the body cavity X ceases, thus resuming relative motion of the tip of the insertion portion 2 with respect to the inner surface of the body cavity X. At this time, as shown by sign C in FIG. 3, the load detected by the load sensor 18 exceeds the peak P, falls suddenly, and then takes a constant value having substantially the same absolute value as the load during the insertion movement.

In other words, in this embodiment, the following decision unit 8 monitors the output of the load sensor 18 and detects resumption of the movement of the insertion portion 2 at the point where the sign of the output reverses. Thereafter, the following decision unit 8 detects resumption of the relative movement of the tip of the insertion portion 2 with respect to the inner surface of the body cavity X at the point where the output from the load sensor 18 exceeds the peak P. Thus, the following decision unit 8 determines that the period from resumption of movement of the insertion portion 2 until the output from the load sensor 18 exceeds the peak P is a non-following period.

Then, even if the insertion length measured by the insertion-length measuring unit 4 changes in the non-following period, the correcting unit 9 cancels the change in the insertion length during the non-following period to perform correction so that the insertion length does not change. Specifically, during the non-following period, the correcting unit 9 sets the change in rotation angle of the motor 15, which the insertion-length measuring unit 4 detects using the encoder 16, to zero. Then, the correcting unit 9 inputs to the insertion-length calculating unit 17 that the rotation angle of the motor 15 is zero, and performs correction so that the measured value of the insertion length itself, measured by the insertion-length measuring unit 4, does not change. In periods other than the non-following period, the correcting unit 9 directly inputs the change in the rotation angle of the motor 15 detected with the encoder 16 to the insertion-length calculating unit 17. In this case, the measured value of the insertion length, measured by the insertion-length measuring unit 4, varies in proportion to the rotation angle of the motor 15.

When a judgment is made by the following decision unit 8 that the non-following period is in effect, the image acquired by the image-acquisition unit 3 is essentially the same, and therefore, the image-acquisition unit 3 stops acquiring images upon receiving a signal from the decision unit 19.

The operation of the thus-configured endoscope apparatus 1 according to this embodiment is described below.

To obtain an image of the interior of the body cavity X using the endoscope apparatus 1 according to this embodiment, the insertion portion 2 is driven by operating the motor 15 to be inserted inside the body cavity X, and the insertion portion 2 continues to be inserted until a prescribed insertion length is measured by the insertion-length measuring unit 4. Then, when the insertion portion 2 is inserted inside the body cavity X to an insertion length in the vicinity of an affected area, the excitation-light light source 10 is operated to radiate excitation light onto the inner wall of the body cavity X via the light guide 11 and the conical mirror 12.

At this time, the image-acquisition unit 3 is operated, for example, at fixed time intervals, and fluorescence generated at the inner wall of the body cavity X due to irradiation with the excitation light is captured by the CCD camera 14 via the conical mirror 12 and the image guide 13. As a result, fluorescence images of the inner wall of the body cavity X are sequentially obtained. Then, the sequentially obtained images are stored in a storage unit 5 in association with the insertion lengths at the moment each image is obtained. Accordingly, it is possible to sequentially obtain images of the inner wall of the body cavity X in the vicinity of the affected area while associating the images with the position thereof in the longitudinal direction of the body cavity X.

In this case, when the insertion portion 2 temporarily stops inside the body cavity X, the inner wall of the body cavity X and the insertion portion 2 become joined due to static friction; therefore, even if the insertion movement is subsequently resumed, for a while, there is a state where the tip of the insertion portion 2 does not relatively move with respect to the inner wall of the body cavity X.

Figure 4:
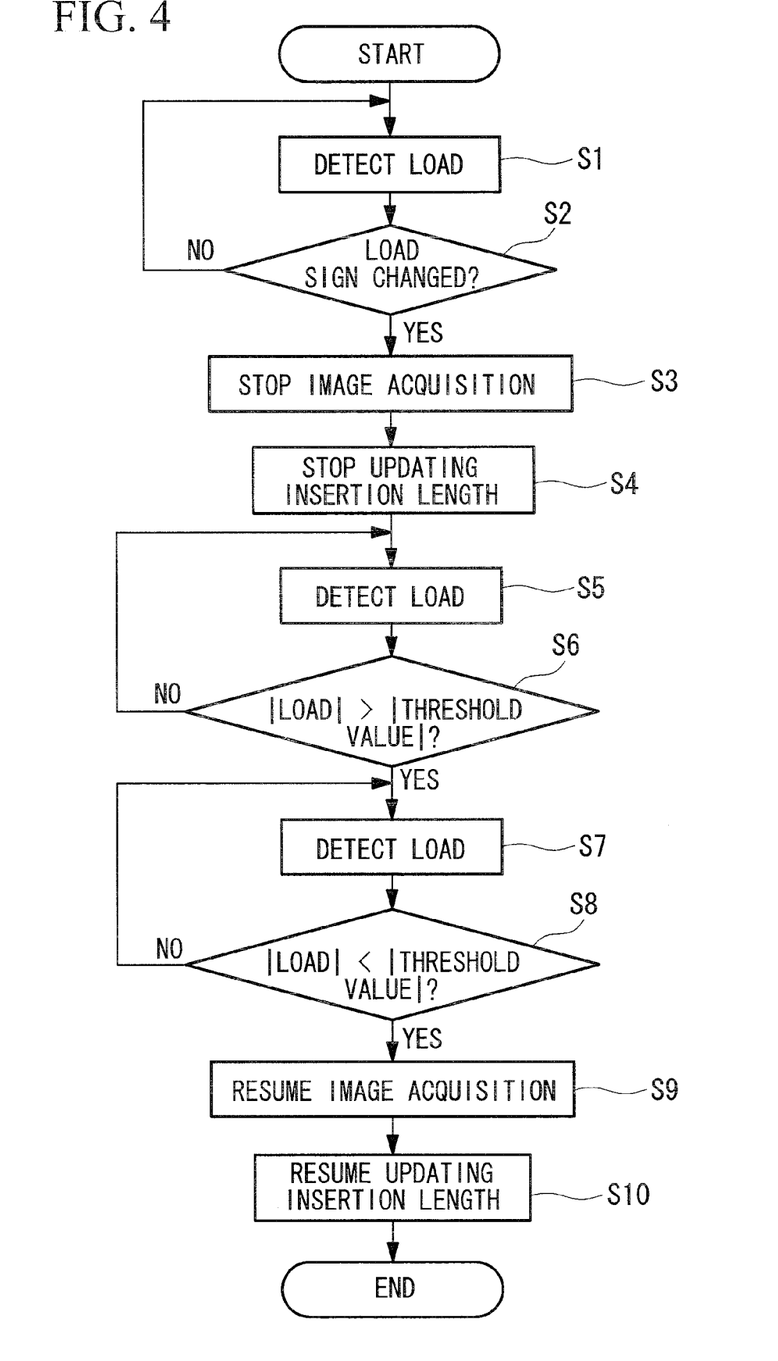
FIG. 4 is a flowchart for explaining following determination in an endoscope-image recording method using the endoscope apparatus in FIG. 1.

With the endoscope apparatus 1 according to this embodiment, as shown in FIG. 4, the following decision unit 8 monitors the output from the load sensor 18 (step S1) and detects the start of reversal of the tip of the insertion portion 2 at the point when the sign of the output reverses (step S2), thus determining that the non-following period has started.

When it is determined by the following decision unit 8 that the non-following period is in effect, acquisition of images by the image-acquisition unit 3 is stopped (step S3). Also, a correction processing unit 7 is operated, and changes in the insertion length measured by the insertion-length measuring unit 4 are cancelled (step S4). In other words, while it is determined by the following decision unit 8 that the non-following period is in effect, the insertion length is not updated.

Then, the following decision unit 8 monitors the output from the load sensor 18 and detects resumption of relative movement of the tip of the insertion portion 2 with respect to the inner surface of the body cavity X at the point when the output exceeds the peak P, thus determining that the non-following period has ended. Specifically, the output from the load sensor 18 is detected (step S5), and it is determined whether or not the output from the load sensor 18 has exceeded a prescribed threshold value (step S6). Thereafter, the output from the load sensor 18 is detected again (step S7), and it is determined whether or not the output falls again below the threshold value after the output has exceeded the prescribed threshold value (step S8). Accordingly, the point when the output from the load sensor 18 falls again below the threshold value is detected as the point when the output from the load sensor 18 exceeds the peak P.

Here, as the threshold value, it is possible to choose a value larger than the absolute value of the kinetic frictional force and smaller than the absolute value of the maximum static frictional force. The threshold value is preferably set to a value obtained by adding the absolute value of the kinetic frictional force and the absolute value of the maximum static frictional force and dividing the total by two. If the threshold value is too large, when the load varies sporadically due to noise, in some cases it may be difficult to accurately determine the point at which the load falls below the threshold value again. In other words, after the load exceeds the threshold value, the load may fall below the threshold value, for example, only one time, due to the influence of noise. In this case, a force that exceeds the maximum static frictional force is not exerted, and therefore, the following period is in effect; nevertheless, falling again below the threshold value ends up being recognized as the end of the following period.

Conversely, if the threshold value is too small, at the point where the load exceeds the threshold value but does not exceed the maximum static frictional force, it may sometimes be difficult to accurately determine the point at which the non-following period ends. In other words, until the maximum static frictional force is exceeded after the threshold value is exceeded, sometimes the insertion portion 2 moves in the opposite direction from the insertion movement. At this time, a force that exceeds the maximum static frictional force is not exerted, and therefore, the following period is in effect;

nevertheless, falling again below the threshold value ends up being recognized as the end of the following period.

The values of the kinetic frictional force and the maximum static frictional force can be measured in advance. It is also possible to use calculated values in the initial insertion movement.

The non-following period is assumed to be from the point where the sign of the output from the load sensor 18 reverses to the point where the load falls again below the threshold value after the prescribed threshold value is exceeded. With this, while the friction between the outer surface of the insertion portion 2 and the inner surface of the body cavity X changes from kinetic friction to zero, variations in the insertion length of the insertion portion 2 detected outside the body cavity X and the amount of movement of the tip of the insertion portion 2 relative to the inner wall of the body cavity X are small. Therefore, the point when the sign of the output detected by the load sensor 18 reverses can be regarded at the start of the non-following period. Similarly, while the friction between the outer surface of the insertion portion 2 and the inner surface of the body cavity X vary from the maximum static friction to the kinetic friction, variations in the insertion length of the insertion portion 2 detected outside the body cavity X and the amount of movement of the tip of the insertion portion 2 relative to the inner wall of the body cavity X are small. Therefore, the point when the load detected by the load sensor 18 falls below the threshold value again can be regarded as the end of the non-following period, in other words, the point when the load exceeds the peak value.

After it is determined by the following decision unit 8 that the non-following period has ended in this way, acquisition of images by the image-acquisition unit 3 is resumed (step S9), and the insertion-length measuring unit 4 resumes adding the insertion-length increment corresponding to the rotation angle increment detected by the encoder 16 (step S10).

Thus, with the endoscope apparatus 1 according to this embodiment, by operating the following decision unit 8, it is determined whether or not the insertion movement of the tip of the insertion portion 2 is following the insertion movement at the base end of the insertion portion 2, and when it is determined that the non-following period is in effect, updating of the insertion length is stopped. Therefore, even if the insertion length changes with the insertion portion 2 remaining joined to the inner wall of the body cavity X, it is possible to reliably prevent storage or display of multiple different insertion lengths in association with the same image.

As a result, when the surgeon performs examination of the interior of the body cavity X during insertion of the insertion portion 2, while viewing the image displayed by the display unit 6, it is possible to accurately associate the insertion length with the image being displayed. Also in the case where the image and insertion length stored in association with each other in the storage unit 5 are displayed afterwards, an advantage is afforded in that it is possible to precisely identify the location of an affected area etc.

In this embodiment, when it is determined by the following decision unit 8 that the non-following period is in effect, the adding of the insertion length by the insertion-length measuring unit 4 is stopped. Instead of this, the insertion length when the non-following period started may be stored, and after the non-following period ends, a new insertion length obtained by subtracting the insertion distance during the non-following period from the measured insertion length may be stored or displayed in association with the image.

In this embodiment, the insertion length is assumed to be measured from the rotation angle detected by the encoder 16 of the motor 15 that drives the insertion portion 2. Instead of this, marks (not illustrated in the drawings) may be provided on the outer surface of the insertion portion 2, and the insertion length may be measured by detecting the marks with a camera (not illustrated in the drawings) etc. at the base end of the insertion portion 2.

Figure 5:
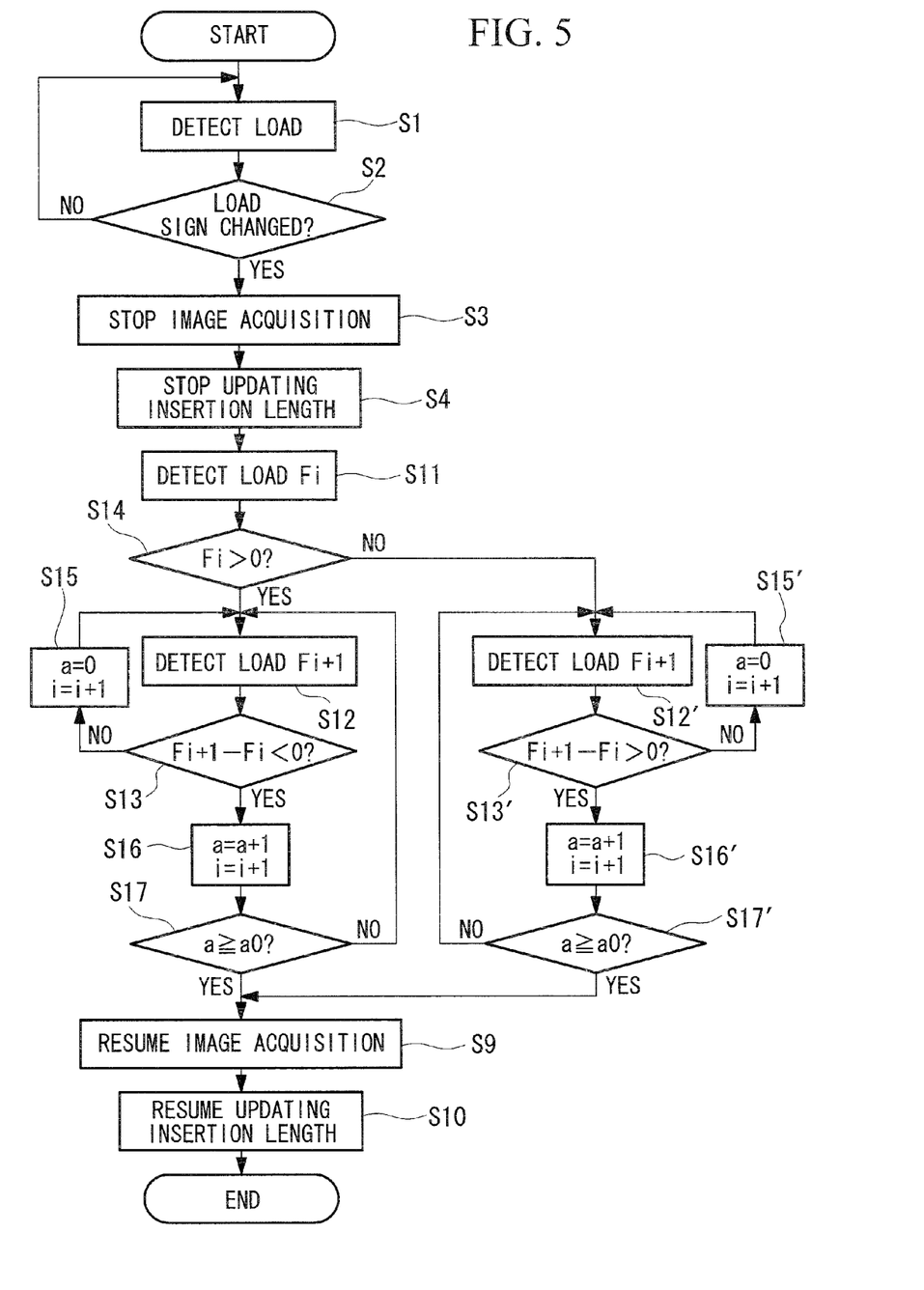
FIG. 5 is a flowchart showing a first modification of the following determination in FIG. 4.

In this embodiment, although the end of the non-following period is determined by the following decision unit 8 by comparing the output from the load sensor 18 with the threshold value, instead of this, the end of the non-following period may be determined upon detecting that the sign of the change in output from the load sensor 18 has reversed after reversing. In this case, as shown in FIG. 5, an i-th load Fi is detected (step S11). Then it is determined whether Fi is positive or negative (step S14). If Fi is positive, the i+1-th load Fi+1 after a time interval is detected (step S12). Then, it is determined whether the difference between the i-th load Fi and the i+1-th load Fi+1, i.e. Fi+1−Fi, goes from positive to negative (step S13). If it does not go to negative, zero is substituted for a, and i is incremented (step S15). Then, the updated i+1-th load Fi+1 is detected again (step S12).

If Fi+1−Fi goes from positive to negative, after a and i are incremented (step S16), it is determined whether or not a is larger than a value a0 which is set in advance (step S17). Here, a is a parameter for detecting the case where Fi+1−Fi sporadically goes from positive to negative due to the influence of noise. a0 can be set in advance to, for example, a0=3, but it is not limited to this value. Accordingly, when, for example, Fi+1−Fi goes to negative only once due to the influence of noise, a≧a0 is not satisfied, and therefore, the load Fi+1 is redetected (step S12).

Here, if Fi+1−Fi merely goes to negative only once and the recalculated Fi+1−Fi is positive, the determination in step S13 is NO. Therefore, zero is substituted again for a, and i is incremented (step S15). On the other hand, if Fi+1−Fi goes to negative three times consecutively, the determination in step S17 is YES. By determining whether or not sign reversal of the load occurs multiple times in this way, the case where the sign changes sporadically due to noise is excluded from the determination.

Because the sign of the load reverses depending on whether the insertion portion 2 is inserted or withdrawn, the sign thereof is determined in step S14 to cope with both cases. In other words, similarly to the above, the load Fi+1 is detected also when it is determined that Fi is negative (step S12'). If Fi+1−Fi is negative, a=0 is substituted, and i is incremented (step S15'). Then, Fi+1 is redetected (step S12'). On the other hand, if Fi+1−Fi is positive, after a and i are incremented (step S16'), it is determined whether a≧a0 (step S17'). If a is smaller than a0, Fi+1 is redetected (step S12'), and if a is equal to or larger than a0, image acquisition is resumed (step S9).

Accordingly, when the insertion movement or the withdrawal movement of the insertion portion 2 is in one direction, it can be detected that the friction produced between the insertion portion 2 and the inner surface of the body cavity X changes from static friction to kinetic friction, and the end of the non-following period can thus be determined. As a result, it is possible to accurately store each position on the inner surface of the body cavity in association with the insertion length.

Instead of steps S15, S15', S16, S16', S17, and S17' described above, as shown in FIG. 6, steps S18 and S18' for determining the end of the non-following period based on the absolute value of the load may be employed. In other words, after it is determined whether the difference between the i-th load Fi and the i+1-th load Fi+1, i.e. Fi+1−Fi, goes from positive to negative (step S13, S13'), it is determined whether the absolute value |Fi+1| is less than the threshold value (step S18, S18').

Figure 6:
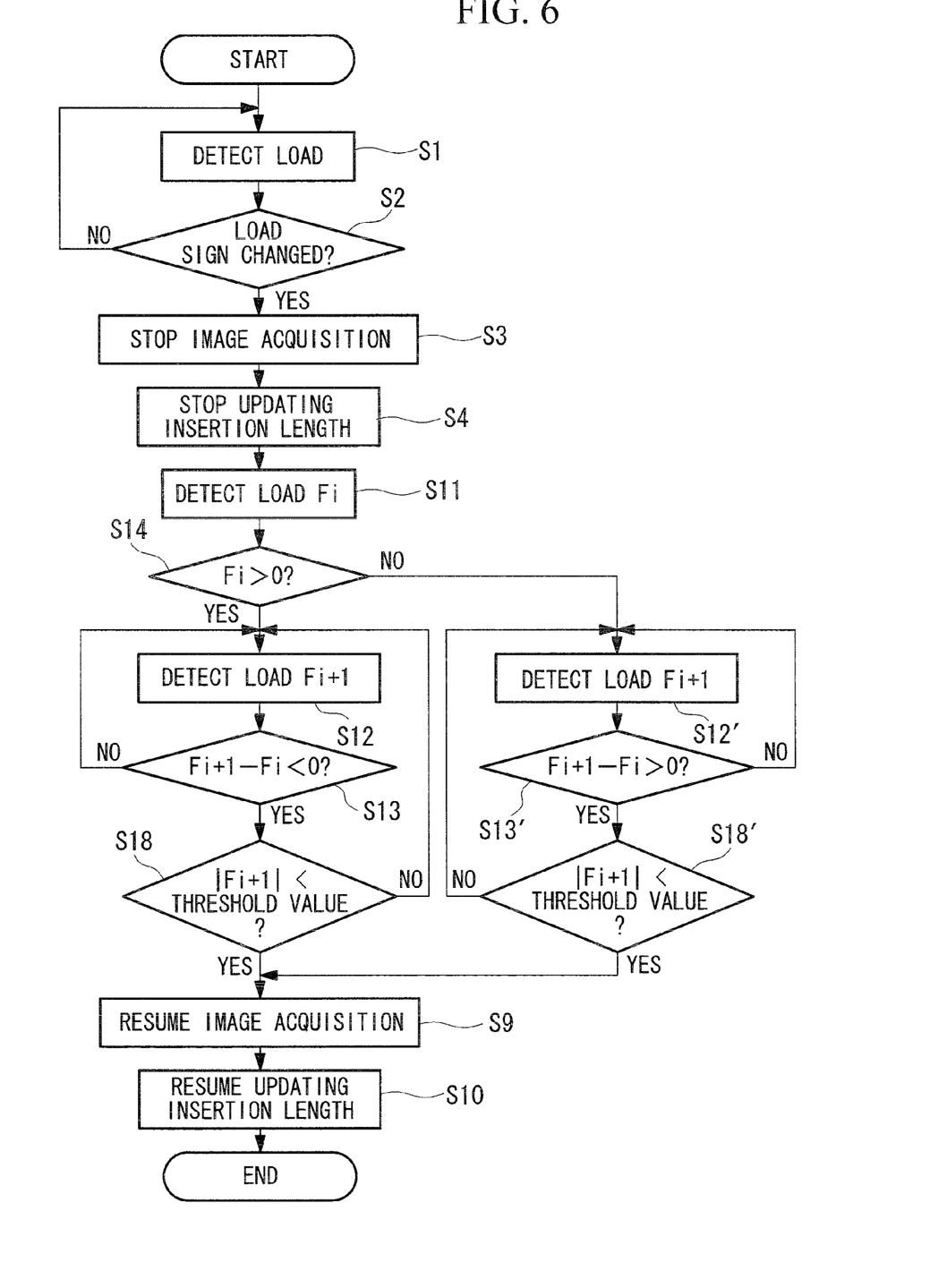
FIG. 6 is a flowchart showing a second modification of the following determination in FIG. 4.

Thus, when the insertion movement or the withdrawal movement of the insertion portion 2 is in one direction, it is possible to detect that the friction produced between the insertion portion 2 and the inner surface of the body cavity X changes from static friction to kinetic friction, and it is thus possible to determine the end of the non-following period. As a result, it is possible to accurately store each position on the inner surface of the body cavity in association with the insertion length.

Figure 7:
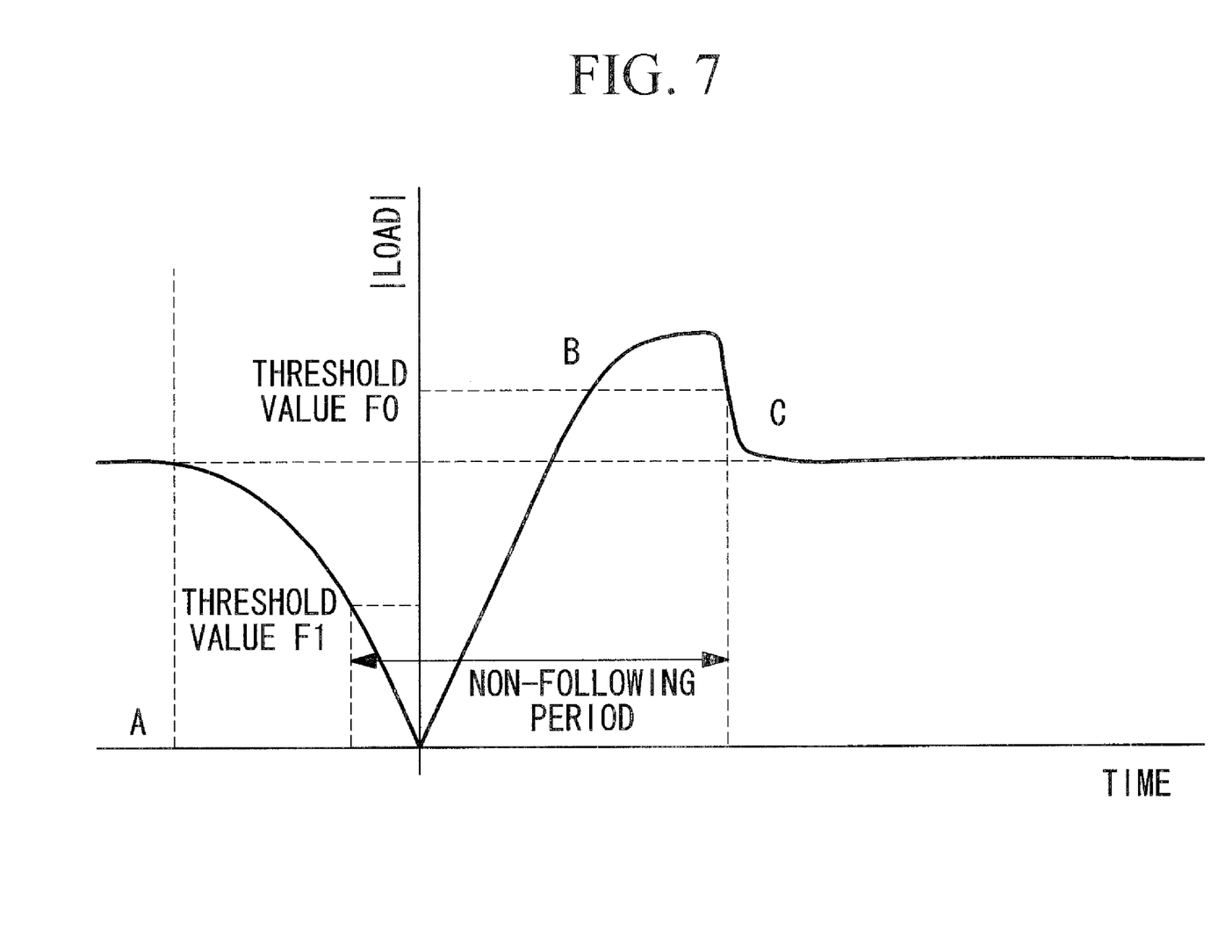
FIG. 7 is a graph showing an example of the absolute value of the load exerted in the longitudinal direction of the insertion portion during the reversing movement in FIGS. 2A, 2B, and 2C, in a third modification of the following decision in FIG. 4.
Figure 8:
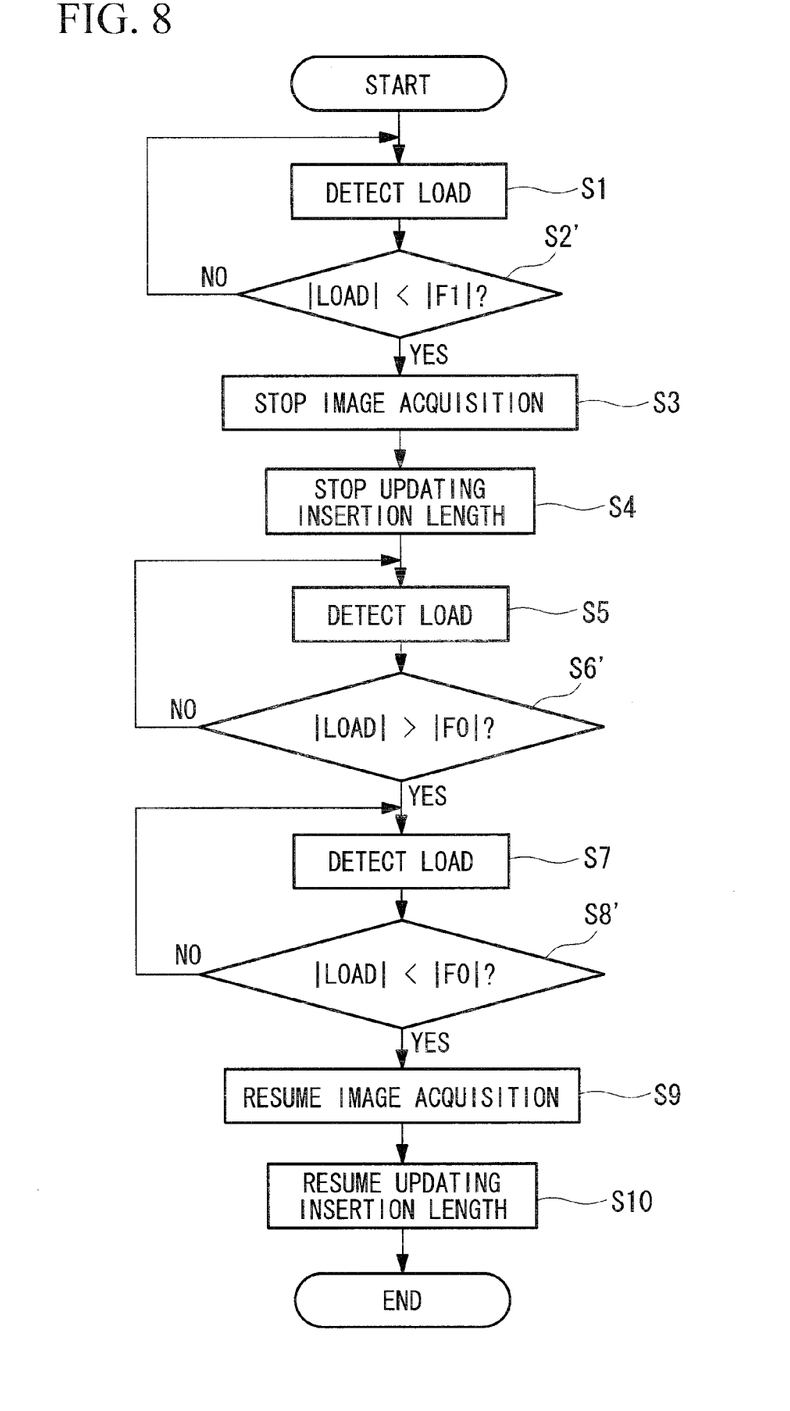
FIG. 8 is a flowchart for explaining following determination using the absolute value of the load in FIG. 7.

As shown in FIG. 7 and FIG. 8, the end of the non-following period may be determined by comparing the absolute value of the load with a prescribed threshold value |F0| (the absolute value of F0) (steps S6', S8'). In this case, as shown in FIG. 8, commencement of the non-following period should be determined when the absolute value of the load falls below a prescribed threshold value |F1| (step S2'). Thus, it is possible to detect that the friction produced between the insertion portion 2 and the inner surface of the body cavity X changes from static friction to kinetic friction, and it is thus possible to determine the end of the non-following period. As a result, it is possible to accurately store each position on the inner surface of the body cavity in association with the insertion length.

Note that the threshold value F0 can be selected similarly to the threshold value described above. For the threshold value F1 on the other hand, a value that is smaller than the absolute value of the kinetic frictional force and larger than zero can be selected. For example, a value obtained by dividing the absolute value of the kinetic frictional force by two may be set as the threshold value F1. If the threshold value is too large, when the load varies sporadically due to noise, in some cases it may be difficult to accurately determine that the friction shifts from kinetic friction to static friction. Conversely, if the threshold value is too small, in some cases it may be difficult to accurately determine the start of the non-following period.

In this embodiment, the image-acquisition unit 3 is operated at fixed time intervals, and excitation light is radiated; instead of this, however, the image-acquisition unit 3 may be operated continuously to acquire fluorescence images.

In this embodiment, the following decision unit 8 determines the non-following period on the basis of the output from the load sensor 18. Instead of this, it may consecutively compare the images continuously acquired by the image-acquisition unit 3 and determine that the non-following period is in effect if there is no change in the images.

During this process, it is possible to more accurately determine the start and end of the non-following period by combining the above-described embodiments. Specifically, the load sensor 18 detects a change in the sign of the load, and thereby the following decision unit 8 determines the start of the non-following period. Thus, when the images that the image-acquisition unit 3 acquires do not change, the following decision unit 8 determines that the non-following period is in effect. Thus, the following decision unit 8 can determine the end of the non-following period based on the image-acquisition unit 3 changing, or based on the output from the load sensor 18 falling again below a threshold value after exceeding a prescribed threshold value, or based on both.

In this embodiment, when it is determined by the following decision unit 8 that the non-following period is in effect, the image-acquisition unit 3 stops acquiring images. Instead of this, the image-acquisition unit 3 may acquire images even in the non-following period, and one image acquired at commencement, termination, etc. of the non-following period may be associated with the insertion length measured by the insertion-length measuring unit 4. Alternatively, in the non-following period, the images that the image-acquisition unit 3 consecutively acquires may be associated with the insertion length whose variation is cancelled by the correction processing unit 7 while updating the images. Accordingly, the image-acquisition unit 3 can acquire images of the interior of the body cavity X even in the non-following period.

In this embodiment, the case where the insertion movement of the insertion portion 2 is reversed has been explained as an example. Instead of this, even if the insertion movement is temporarily stopped, followed by resumption of insertion in the same direction, because the friction between the insertion portion 2 and the inner wall of the body cavity X changes from static friction to kinetic friction, it is possible to perform processing similarly to this embodiment. Specifically, in step S2 in FIGS. 4 to 6, the following decision unit 8 monitors the output from the load sensor 18 and detects whether or not the output is zero. Then, at the point where the output becomes zero, the following decision unit 8 detects that the insertion portion 2 has stopped, which can be judged as commencement of the non-following period.

When the following decision unit 8 determines that the non-following period is in effect by monitoring the output from the load sensor 18, acquisition of images by the image-acquisition unit 3 is stopped (step S3). In subsequent steps, similarly to the embodiment described above, the following decision unit 8 detects resumption of relative movement of the tip of the insertion portion 2 with respect to the inner surface of the body cavity X at the point where the output exceeds the peak P. Thus, the following decision unit 8 can determine that the period from stopping of the insertion portion 2 until the output from the load sensor 18 exceeds the peak is the non-following period. In cases where it is difficult to determine whether the output from the load sensor 18 is zero, so long as the load is a prescribed value or lower, the output from the load sensor 18 may be regarded as being zero.

In this embodiment, a case where a side-view optical system, like the conical mirror 12, is at the tip of the insertion portion 2 has been described as an example; instead of this, however, the present invention may be applied to an endoscope apparatus having a normal optical system for observing in the forward direction of the tip of the insertion portion 2.

In this embodiment, a sensor that is built into the motor 15 is used as the load sensor 18; instead of this, however, a load sensor that is connected to the base end of the insertion portion, either directly or via an elastic member, may be employed.

The invention claimed is:

1. An endoscope apparatus comprising:
   an insertion portion for insertion into a body cavity;
   an image-acquisition unit that acquires an image of the inside of the body cavity at a tip of the insertion portion;
   an insertion-length measuring unit that is disposed at a base end of the insertion portion and that measures an insertion length of the insertion portion inside the body cavity;
   a storage unit that stores the image acquired by the image-acquisition unit in association with the insertion length measured by the insertion-length measuring unit;
   a following decision unit that determines whether insertion movement at the tip of the insertion portion follows insertion movement at the base end of the insertion portion;
   a correcting unit that corrects the insertion length of the insertion portion associated with the image acquired by the image-acquisition unit so as to cancel a change in the insertion length measured by the insertion-length measuring unit in a period where the insertion movement at the tip does not follow the insertion movement at the base end, on the basis of a determination result from the following decision unit.

2. An endoscope apparatus according to claim 1, wherein the following decision unit includes a load detecting unit that detects a load exerted in the longitudinal direction of the insertion portion, and
after movement of the insertion portion in the longitudinal direction stops, when movement resumes in the same direction as the movement, or in the reverse direction thereto, and the load detected by the load detecting unit becomes a peak value, a period from resumption of movement of the insertion portion until the load exceeds the peak value is determined to be a period where the insertion movement at the tip does not follow the insertion movement at the base end.

3. An endoscope apparatus according to claim 2, wherein the following decision unit detects resumption of movement of the insertion portion when the sign of the load detected by the load detecting unit changes.

4. An endoscope apparatus according to claim 1, wherein the following decision unit compares images consecutively acquired by the image-acquisition unit, and if, as a result of the comparison, the images do not change, when the insertion length measured by the insertion-length measuring unit changes, determines that the insertion movement at the tip of the insertion portion does not follow the insertion movement at the base end of the insertion portion.

5. An endoscope apparatus according to claim 1, wherein the image-acquisition unit is provided with a side-view optical system that collects light from radially outward of the insertion portion.

6. An endoscope-image recording method for storing an image of the inside of a body cavity, which is acquired by an image-acquisition unit at the tip of an insertion portion that is inserted inside the body cavity, in association with an insertion length of the insertion portion inside the body cavity, which is measured at the base end of the insertion portion, comprising:
determining whether insertion movement at the tip of the insertion portion follows insertion movement at the base end of the insertion portion; and
correcting the insertion length associated with the acquired image so as to cancel a change in the insertion length measured in a period where the insertion movement at the tip does not follow the insertion movement at the base end, on the basis of the determination result.

7. An endoscope-image recording method according to claim 6, further comprising:
detecting a load exerted in the longitudinal direction of the insertion portion; and
after movement of the insertion portion in the longitudinal direction has stopped, when movement resumes in the same direction as the movement, or in the reverse direction thereto, and the detected load becomes a peak value, determining that a period from resumption of movement of the insertion portion until the load exceeds the peak value is a period in which the insertion movement at the tip does not follow the insertion movement at the base end.

8. An endoscope-image recording method according to claim 7, wherein resumption of movement of the insertion portion is detected when the sign of the detected load changes.

9. An endoscope-image recording method according to claim 7, wherein consecutively acquired images are compared, and if, as a result of the comparison, the images do not change, when the measured insertion length changes, it is determined that the insertion movement at the tip of the insertion portion does not follow the insertion movement at the base end of the insertion portion.

* * * * *